United States Patent [19]

Kurtz

[11] Patent Number: 4,723,911
[45] Date of Patent: Feb. 9, 1988

[54] INTELLIGENT DENTAL DRILL

[75] Inventor: John L. Kurtz, Indiana, Pa.

[73] Assignee: University of Pittsburgh, Pittsburgh, Pa.

[21] Appl. No.: 796,913

[22] Filed: Nov. 13, 1985

[51] Int. Cl.$^4$ .............................. A61C 1/00; A61C 3/00
[52] U.S. Cl. .......................................... 433/27; 408/9; 408/16
[58] Field of Search .......................... 433/131, 132, 27; 408/8, 9, 16, 6; 318/313

[56] References Cited

U.S. PATENT DOCUMENTS

| | | | |
|---|---|---|---|
| 3,446,099 | 5/1969 | Lesher et al. | 408/16 |
| 3,514,679 | 5/1970 | Larsen | 318/313 |
| 4,340,326 | 7/1982 | Buonauro et al. | 408/16 |
| 4,459,523 | 7/1984 | Evans et al. | 318/313 |
| 4,493,643 | 1/1985 | Tachibana | 433/27 |
| 4,502,823 | 3/1985 | Wronski et al. | 408/6 |

FOREIGN PATENT DOCUMENTS 6004  1/1983  Japan .................................. 318/313

OTHER PUBLICATIONS

Junghans, Speed Controller for Motors, Aug., 77, p. 32.

Primary Examiner—Z. R. Bilinsky
Attorney, Agent, or Firm—Reed Smith Shaw & McClay

[57] ABSTRACT

An apparatus for conducting high-speed drilling bone tissue of varying density causing proportioned variations in the speed of the drill bur. A means is provided for automatically sensing the momentary bur rotational speed and producing either a visual or audible signal represented of the changing speed and its companion density.

6 Claims, 9 Drawing Figures

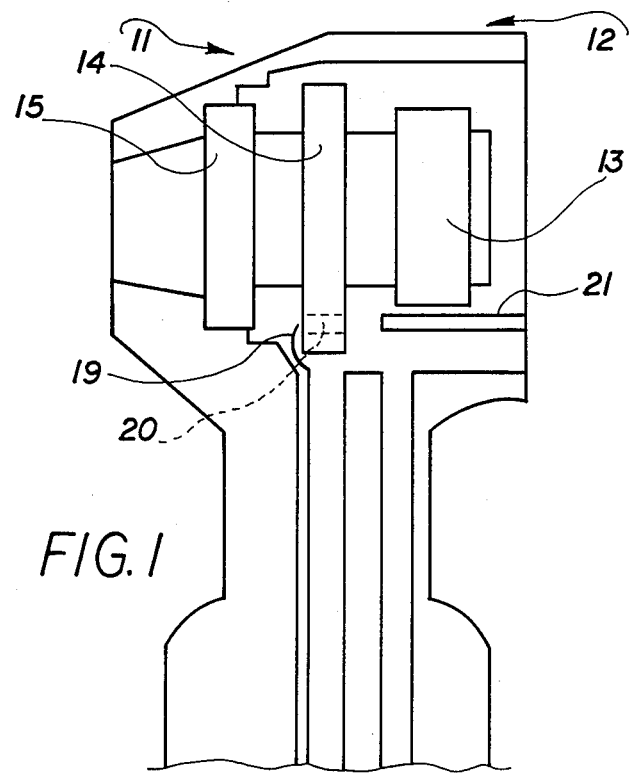
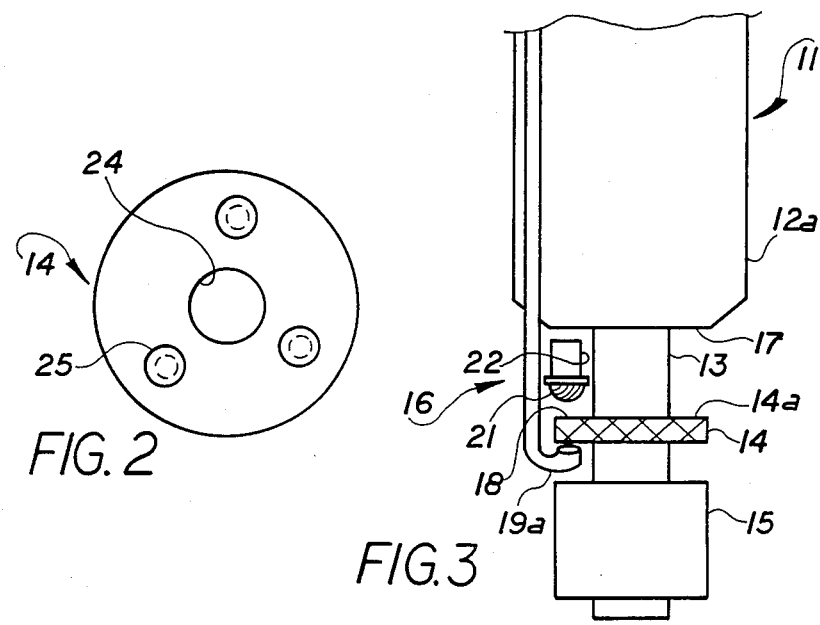

INTELLIGENT DENTAL DRILL

FIELD OF THE INVENTION

The present invention relates to a dental/surgical drilling handpiece having a rotational speed detection device.

BACKGROUND OF THE INVENTION

For dental drilling of bone tissue, a tool tip or bur on the head of a handpiece is rotated at a high speed. However, when the cutting load increases, rotating speed is reduced significantly. To measure the rotating speed under varying load is desirable for proper treatment, useful for data analysis of clinical experiments, and necessary to control the rotating speed at a constant value. Measurement of speed variation is a requisite to activating any automatic feedback feature for spontaneous modification of the power input to the motor. For these purposes, prior art attempts to detect the rotating speed of the motor for a micro-motor driven handpiece were based upon motor drive voltage or current. However, this attempt has not been successful, since the rotating speed is detected indirectly via voltage or current, and thus large errors are caused.

One attempt to bypass the shortfalls of the described motor drive voltage approach is a magnetic speed detection system as described in Tachibana U.S. Pat. No. 4,493,643 granted Jan. 15, 1985. While this is a non-contact rotating speed detection device, based on an electromagnetic induction pulsed generator, the electronic complexity, the special materials required, and the complex handpiece redesign make this system economically unattractive for general professional dental use.

OBJECTS OF THE INVENTION

It is, therefore, an object of the present invention to provide a dental handpiece free from the problems or drawbacks as noted above. It is another object to provide a non-contact rotational speed detection device that requires only a minimal modification of the existing dental handpieces to achieve rotary speed monitoring and the desired control feature. It is still another object to provide an optical-electrical speed detection system which can interface directly with a computer processing module that provides almost instaneous readout as to the variable density of the materials being drilled. A still a further object is a detection system that compels little or no modification to the exterior of a standard handpiece, preferably leaving the drill size and handpiece shape unaltered in its established configuration.

SUMMARY OF THE INVENTION

According to the invention, by utilizing the fact that the drilling bit (burr) rotational speed is directly related to the density (hardness) of the material being bored, there is provided a means for sensing the momentary bur rotational speed and producing either a visual or audible signal representative of such changing speed and its companion density. The variable rotational speed is sensed using a speed and encoder component which functions by producing an interruptable light beam that is sensed continuously by a visible light detector, such as a photodiode. Mechanical means such as a perforate wheel, is provided on the rotating power shaft that drives the bur, which will interrupt the light beam with a frequency that is in direct correlation to the speed of the shaft. The "light break" frequency can be one per revolution, or a multiple thereof, depending upon the accuracy of the detection function required.

Every time the beam is interrupted, the voltage transmitted from the light detector component is measurably reduced. The system can be measurably arranged such that when the beam impinges on the photodiode, it produces at the monitoring terminal the digital "one" and when interrupted, it yields a digital "zero". Due to the inherent features of the encoder, typically a photodiode, very fast (down to nanoseconds) responses of the detector system can be achieved.

In one preferred embodiment, a turbine wheel, normally pinned to the rotating shaft, can be modified to function as the light beam interruptor. There is next provided a means for transducing the optical beam signal into an electrical signal, which typically is a modified sinusoidal wave, and modifying that electrical signal so that it passes through a zero voltage level; and means for converting the modified sine wave signal into a square wave signal that is suitable for input to a digital counter. Next, means for counting and recording the frequency of the square wave signal are provided. In one embodiment, the digital output is converted to a visual display means indicative of the momentary rotation speed of the drill bur. A number of encoder configurations, as will be described herein, can be utilized to provide the handpiece surgeon with useful information on the bur operation during use.

BRIEF DESCRIPTION OF THE DRAWINGS

FIG. 1 is a schematic side view of the operating head of a dental handpiece modified according to a first embodiment of the present invention.

FIG. 2 is the top plan view of a turbine wheel normally secured to the dental handpiece drive shaft which has been modified to serve in the present invention;

FIG. 3 is a schematic of an neurological drill modified to support an alternate embodiment of the signal encoder assembly;

DETAILED DESCRIPTION OF THE INVENTION

Figure 3A:
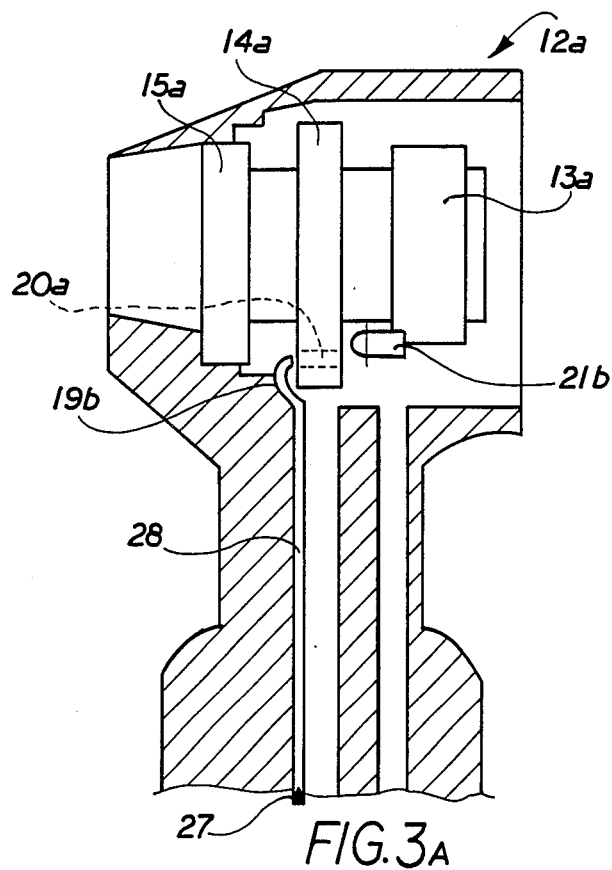
FIG. 3a is a schematic side view of an operating head modified to utilize an LED as a beam emitter.

Referring now to FIG. 1, shown is a first embodiment of the present invention when applied to a conventional pneumatically driven, dental handpiece, generally 11, and comprising the stationary drilling housing 12, an inner rotary shaft 13 and an annular-shaped turbine wheel 14 pinned to shaft 13, positioned with in the housing 12 and the mounting fixture 15 for a drill bur. A first optical fiber cable 21 transmits the light beam through a turbine wheel perforation (not seen) while opposing fiber cable 21 detects and transmits the modified signal. The cables may be as small as 50 microns in diameter and thus can be conveniently threaded through the handpiece airline.

While it is desired to employ fiber cables of the smallest diameter that will function in the described setting, the minimum amount of light power that is needed to actuate the optical detection system has defined the practical limit on cable diameter reduction. If one emitter cable 19 is about 100 micrometers (microns) in diameter, then the other detector cable 21 should be at least 200 microns in diameter to insure an adequate amplitude for the light beam. These minimum dimensions can be interchanged between the opposing cables as design considerations dictate.

The optical cable system encodes the rotational speed in this embodiment, except it is postulated that the detector cable may preferably be the one positioned without the bend to preclude any possible distortion of the transmitted signal. The signal processing and conversion means to use the data is identical in both embodiments and will shortly be described.

Referring to FIG. 2, the conventional turbine wheel 14 of a dental handpiece which has been modified to function as an encoder element is seen. The existing equipment has equispaced bores 25a, 25b and 25c, which may need to be counterbored to ensure a sufficient time interval for the light beam to trigger the detector (not seen), while the wheel itself averages about 9 mm. in diameter, the light holes need only be about one tenth of that diameter, or about 1 mm. Central bore diameter 24 is conformed so as to press fit on the drill shaft. An alternative approach to turbine wheel adaption will be described in relation to FIG. 4.

In FIG. 3 is presented a schematic of a drill employed in neurological practice and also employing an alternate means of signal detection and encoding. Depicted is a high resolution, optical-reflective, encoder assembly 16, securely mounted on the undersurface 17 of housing 12a. It is typically a photodiode detector. Spaced apart (with only the annula of periphery 18 of wheel 14a being interposed) is the light emitter component 19a, which directs a continuous light beam that is focused on the sensor element lens 21b of detector 22. One commercially available detector assembly able to effect this result is the PIN photodiode series 5082-4200 of the Hewlett-Packard Company, which is a focused detector comprising a silicon planar device that is adapted for visible light and near infrared range radiation. Its utility in high speed tachometry and fiber-optic detection has been confirmed in the present invention. The speed of response is less than one nanosecond, and the frequency response extends from dc to 1.0 GegaHertz. For example, the photodiode unit 5082-4205 is a low capacitance Kovar and ceramic package of small dimensions with a hemispherical glass lens.

The emitter component 19a is conveniently a fiber-optic cable that is adapted to be laid in a vertical peripheral groove added to the housing, which groove is typically about 0.1 millimeters in cross-section. The actuation speed and detection functions of the signal conversion assembly will be described in detail below.

In another embodiment, a low-cost encoder configuration has been developed (not shown). A PIN photodiode 21b is placed in the end cap at the rear of the drill, and serves as the detector. It is connected to the remaining electronics by a coaxial cable FIG. 3a, which can be inset as described above. A Light Emitting Diode (LED) 27 is then fastened to one end of the 50 μm (micron) diameter cable 28. The other cable end 19b, aligned with the turbine hole 20a, emits a beam of light which shines on the PIN detector. It is interrupted by the turbine wheel's motion. This LED/optical cable functions as the beam emitter and should be of sufficient power in cooperation with a photodiode detector.

The photodiode like that shown in FIG. 3 can be placed inside the end piece of the drill. It can be screwed or snapped into place. It will require modification to the end piece 13a to accomodate same, but none to the other standard drill components. FIG. 3a depicts a schematic vertical section view of the operating modified to operate per this embodiment.

Figure 4:
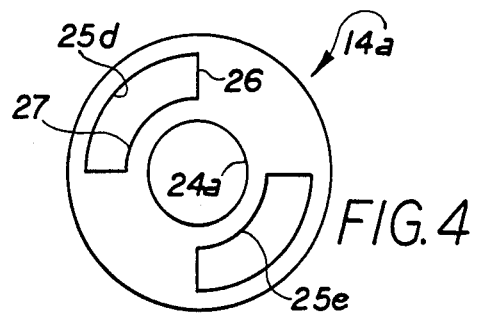
FIG. 4 is a top plan view of an encoder code wheel adapted for mounting on the neurological drill embodiment of FIG. 3.

Referring to FIG. 4, the turbine wheel 14a as modified to function as an encoder element, is seen. The central circular orifice 24a accommodates the rotor shaft 13a seen in FIG. 2, while two arc-like slots 25d and 25e are inscribed in the solid portion of the wheel. In this embodiment, for each revolution of the shaft, light will thus reach the detector element for an interval ranging up to 400 nanoseconds, contingent on the variable rotary speed of the shaft. This aperture length is clearly sufficient to actuate the monitoring circuitry, given its fast response time.

Calculations have shown that the creation of the symetrically-located slots even when taking up as much as two quadrants of the wheel 14a, do not create any vibrational imbalance for the fast spinning wheel. These slots yield a more uniform moment of inertia and would be less prone to affect the drilling action. The encoding wheel 14a dimensions are typically an outer diameter of 9 millimeters, an inner bore 24a of about 4.95 millimeters, a thickness of 1 millimeter and a slot width 26 of 2 millimeters, extending along an arc 27 of as much as 90°.

Figure 5A:
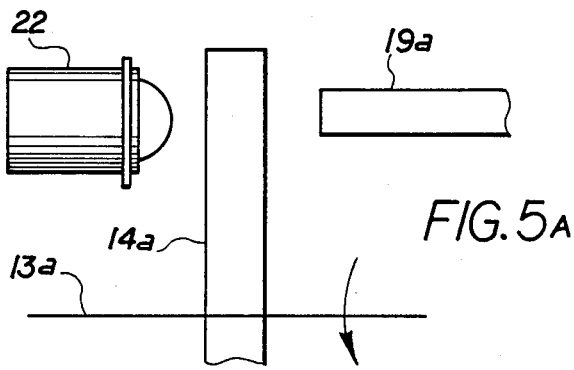
FIGS. 5a and 5b are schematic views of how the encoding wheel functions to generate an interruptable light beam to the optical signal detection system.
Figure 5B:
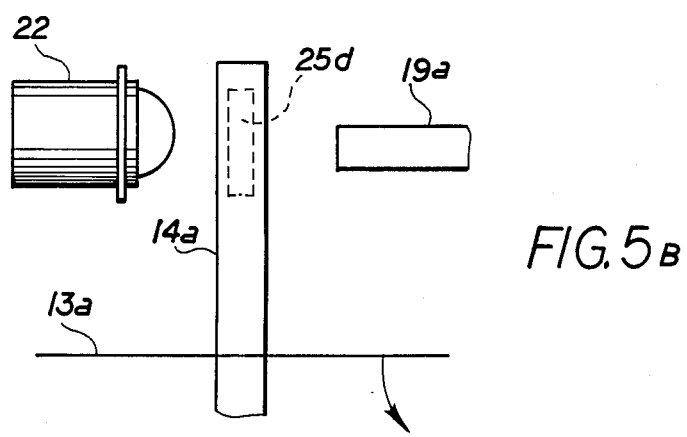
Figure 6:
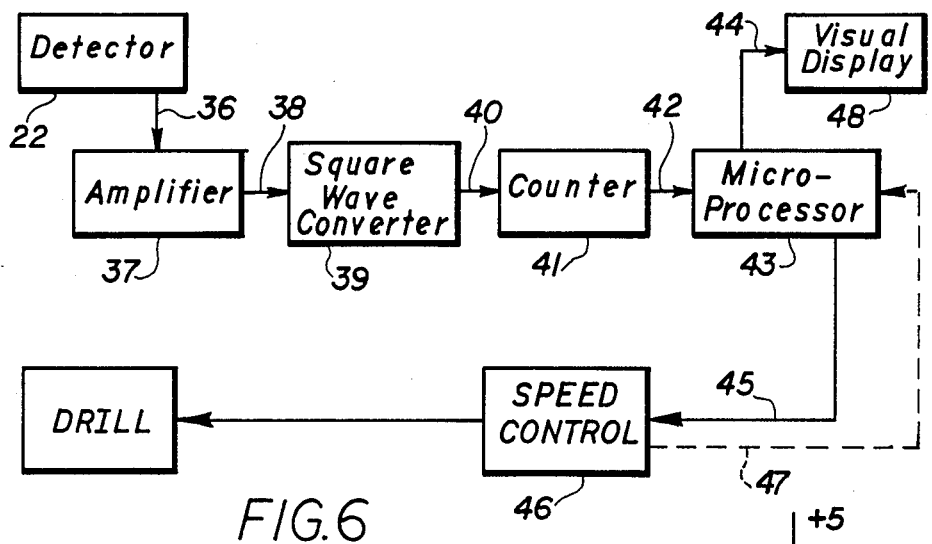
FIG. 6 is a block diagram of the functional interrelationship of the modified handpiece drill, the rotational frequency detector/encoder, the central microprocessor and the feedback circuit for the power (speed) control to the handpiece drilling shaft.

In FIGS. 5A and 5B are seen schematically how the embodiment of FIGS. 1 encodes the interplay of the light signal and the rotating turbine wheel 14a. In the embodiment of FIG. 5a, while the imperforate portion of wheel 14 is interposed between them, the beam from emitter 19 does not reach the photodiode 22. Thus, no voltage is generated at detector 22 while the wheel is so positioned, and no current is being delivered to a monitoring and signal processing circuit shown and now described in relation to FIG. 6. However, when the light beam does reach photodiode 22, (FIG. 5B) current flows creating a voltage during the beam contact interval through slot 25d. That voltage signal 36 generated by detector 22 is amplified by amplifier 37, if necessary, to a value needed to activate the remaining circuitry. Additionally, any DC off-set in voltage signal 36 is eliminated by standard biasing techniques. The amplified signal 38 is passed through square wave converter 39 to generate a neat, clean signal 40 capable of activating digital counter 41. Digital counter 41 counts and stores this encoder signal and outputs it for processing by microprocessor 43.

An experiment was conducted to ascertain the feasibility of a turbine-mounted encoder using a laser beam as a coherent light beam emitter. A laser was positioned on one end of the drill turbine (rear), while a 50 micron optical cable was aligned with the laser and turbine hole just as seen in FIG. 1.

As the turbine was turned, and the hole 20 was allowed then to interrupt the beam, the detector turned on when the hole was aligned, and off when the aperture was not aligned.

This work established that the encoder detection will work with the existing size turbine hole. However, the current cost of a laser which can transmit sufficient power makes this embodiment commercially less desirable than using a PIN photodiode in the end cap.

Microprocessor 43 takes signal 42, which is an encoded signal of the frequency. The frequency, of course, is related to the speed of rotation of the drill. By inverting signal 42, and performing other minor signal processing functions, microprocessor 43 generates a speed of rotation signal 44 which can be displayed on display 48 for the dentist to see or which can activate an audio generator. Additionally, further signal processing can be done by microprocessor 43 to generate a speed control signal 45 which operates the drill at the desired speed.

Typically, the drill is operated by compressed air. Speed control 46 is an air pressure valve (not seen) which controls the rotational speed of the drill depending upon the air pressure. Speed control signal 45 varies the air pressure and, thus, the speed of the drill shaft.

In a preferred embodiment, microprocessor 43 monitors the air pressure of speed control 46. This monitoring signal 47 is converted by an A/D converter (not shown) into a signal the microprocessor can use. Microprocessor 43 then performs a simple routine to determine if the drill is operating in the same medium. It first measures initial values for the air pressure and the drill speed. Second, it measures the air pressure from signal 43 and then measures the speed of the drill using signal 42 from the detector circuit. Microprocessor 43 then calculates the change in air pressure. If there is a change in air pressure, the microprocessor can turn on a light or generate an audio signal to indicate this to the dentist. Typically, a change in air pressure occurs during start-up or shut-down of the drill.

If no change in the air pressure is detected, microprocessor 43 calculates the change in speed of the drill. If there is no change, the drill is still operating in the same medium and microprocessor 43 returns to the second step above. The measuring or sampling just described is done preferably every half second but could be done at a higher rate, such as 1000 times per second.

If, however, there is a change in the speed of the drill, this indicates that the drill is now operating in a different medium with a different density. Microprocessor 43 can then send speed control signal 45 to speed control 46 to adjust the speed of the drill and generate speed of rotation signal 44 to inform the dentist that the drill is now operating in a different medium.

In a preferred embodiment, signal 36 produced by detector 22 is shaped like a modified sine wave. Amplifier 37 only increases the magnitude of signal 36, it does not change its shape. Thus, square wave converter 39 is needed to convert amplified signal 38 to a square wave signal 40 which can be inputted into binary counter 41. Square wave converter 39 can be as simple as the commonly available Schmidt trigger, such as Texas Instruments (TI) 7421. Similarly, counter 41 can be made from a series of 8-bit counters cascaded together, such as Texas Instruments 7490. The output from the 8-bit binary counters can be fed to a latch, typically a Texas Instruments 6821 PIA, where it is held for use by microprocessor 43.

Figure 7:
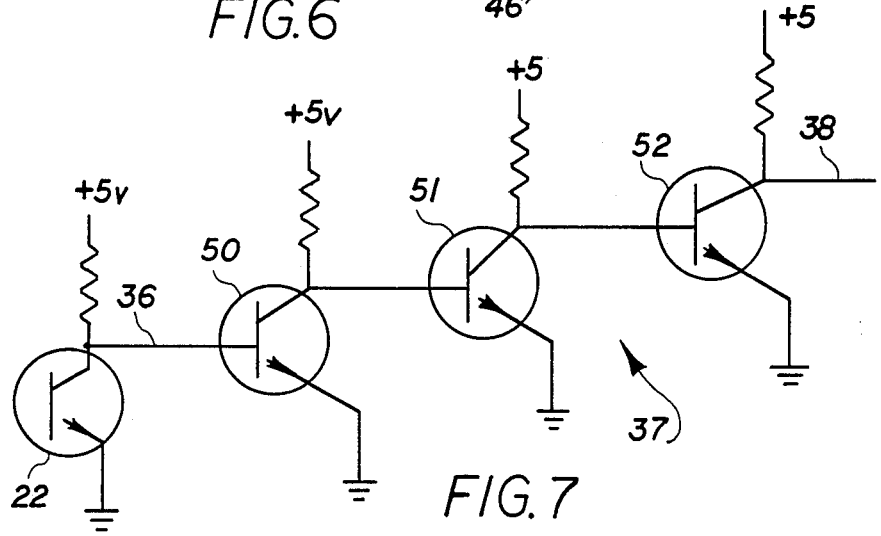
FIG. 7 is a typical embodiment of the detector and amplifier circuits shown in FIG. 6.

FIG. 7 shows a typical embodiment of the circuits for detector 22 and amplifier 37 used when the light source is a laser and detector 22 is placed at the end of a fiber optic cable. Detector 22 is a Motorola MFOD73 pin photodiode. When light is detected by detector 22, the diode turns on and sends a voltage signal 36 to the base of transistor 50. A voltage as low as 0.5 V. is adequate to turn on transistor 50. Biasing of detector 22 may or may not be necessary to eliminate any DC Offset. Transistor 50, along with transistors 51 and 52, are in the common-emitter configuration and, if decreasing amounts of resistance are used in the collector-resistor, the signal 36 will be amplified. The transistors are common ones known to those skilled in the art. Transistors 50 and 51 are TI 2n3704 and transistor 52 is an Hewlett-Packard (HEP) 50015.

Another preferred embodiment uses Texas Instruments (TI) 747 op amplifier, as amplifier 37, particularly when the light source is a light emitting diode (LED) and the detector is placed at the end of a fiber optic cable. Again, detector 22 is a Motorola MFOD73 PIN photodiode. In this embodiment, the amplifier can provide any biasing necessary to zero detection signal 36.

Depending upon the source of the light beam and detector used, there may or may not be a need for amplifier 37 and/or square wave generator 39, as the signal from detector 22 may be sufficient to activate counter 41. For example, if detector 22 is a Motorola MRD14B, no amplifier is necessary. The light falling on this photodiode is sufficient to generate a signal capable of activating square wave generator 39. With proper adjustment and biasing, signal 36 from this detector can even be fed directly into counter 41 without passing through square wave generator 39. (Not shown)

Utilizing the microprocessor as just described, coupled with a programmable time, the r.p.m.'s of the bur shaft can be determined down to 0.01 seconds. The r.p.m. reading will reflect whether the surgeon is operating in dental decay or tooth enamel. These readings are on an order of magnitude of different density from one another, and specifically a significant change in r.p.m. will be displayed when the bur leaves decay and encounters the much harder enamel.

The present invention can be embodied in various handpieces such as a straight type whose output shaft is installed in the longitudinal direction of the handpiece, whether it is of the electrical drive or the pneumatic drive method. The system is durable and inexpensive, being shown to accurately detect rotating speed under abruptly varying loads, and thus useful in the dentist training, clinical experiments and various treatments.

While presently preferred embodiments of the present invention have been described in particularity with reference to the drawings, the invention may be otherwise embodied within the scope of the appended claims.

What is claimed is:

1. In an apparatus for high-speed drilling of bone tissue, wherein varying tissue densities cause proportional variations in the rotational speed of the drill bur, the improvement comprising means for promptly sensing the momentary drill rotational speed and producing a processable signal representative of that speed further comprising:
   (a) first means for emitting a detectable continuous light beam in a direction substantially parallel to the drive shaft of a drilling assembly;
   (b) second means within the assembly providing for intermittent and regular interruption of the light beam, the frequency of which is indicative of the rotational speed of the shaft which further comprises a turbine wheel secured to said shaft which is perforated partially along the circular path thereof such that it intersects the light beam;

(c) third means for detecting the frequency of interruption of said light beam and converting the frequency into an electrical signal which further comprises an optical fiber serving as a pathway for the light emitting means and a photodiode serving as a detector;

(d) fourth means for counting and recording the frequency of the electrical signal from the detecting means;

(e) fifth means for outputting the digital output to a visual display means indicative of the momentary rotational speed of the drill while passing through bone tissue; and (f) a sixth means provided for converting the electrical signal to a digital form which is adapted to be stored by a signal microprocessor means, whereby controlled penetration of human tissues with minimal damage to healthy tissues is achieved.

2. The apparatus of claim 1 wherein the first means for emitting a detectable beam is a first optical fiber serving as the pathway for the light emitting means and the third means is a second optical fiber serving as the detector.

3. The apparatus of claim 1 wherein the electrical signal is modified by a seventh means to produce a second signal that passes through a zero voltage level; and an eighth means for converting the second signal to a third squared wave signal suitable for input to a digital counter, and said fourth means being adapted to process said squared wave signal.

4. The apparatus of claim 1 wherein the first means is a first optical fiber and the third means is a PIN photodiode detector.

5. The apparatus of claim 1 wherein the sixth means is a square wave converter.

6. The apparatus of claim 1 wherein the first means is a light emitting diode coupled with a first optical fiber cable and the third means is a PIN photodiode detector.

* * * * *